United States Patent [19]

Ray et al.

[11] Patent Number: 5,127,912
[45] Date of Patent: Jul. 7, 1992

[54] SACRAL IMPLANT SYSTEM

[75] Inventors: R. Charles Ray, 5425 - 87th Ave. West, Tacoma, Wash. 98467; Richard B. Ashman, Dallas, Tex.

[73] Assignee: R. Charles Ray, Tacoma, Wash.

[21] Appl. No.: 593,196

[22] Filed: Oct. 5, 1990

[51] Int. Cl.$^5$ .......................... A61F 5/01; A61F 2/44; A61F 5/00
[52] U.S. Cl. ........................................ 606/61; 623/17
[58] Field of Search ............... 606/61; 623/17; 128/69

[56] References Cited

U.S. PATENT DOCUMENTS

| | | | |
|---|---|---|---|
| 4,641,636 | 2/1987 | Cotrel | 128/69 |
| 4,719,905 | 1/1988 | Steffee | 128/69 |
| 4,743,260 | 5/1988 | Burton | 623/17 |
| 4,773,402 | 9/1988 | Asher et al. | 128/69 |
| 4,950,269 | 8/1990 | Gaines, Jr. | 606/61 |

FOREIGN PATENT DOCUMENTS 0301489  7/1988  European Pat. Off. .

OTHER PUBLICATIONS

Roy-Camille, Raymond et al., "Internal Fixation of the Lumber Spine with Pedicle Screw Plating," *Clinical Orthopedics & Related Research*, No. 203 (Feb. 1986), pp. 7-17.
Shipman, Pat et al., "The Human Skeleton," *Harvard University Press*, Cambridge, Massachusetts, and London, England (1985), pp. 81-93.
Asher, Marc A. et al., "Anthropometric Studies of the Human Sacrum Relating to Dorsal Transsacral Implant Designs," *Clinical Orthopaedics and Related Research*, No. 203 (Feb. 1986), pp. 58-62.
Roy-Camille, Raymond et al., "Internal Fixation of the Lumbar Spine with Pedicle Screw Plating," *Clinical Orthopaedics and Related Research*, No. 203 (Feb. 1986), pp. 7-17.
Louis, Rene, "Fusion of the Lumbar and Sacral Spine by Internal Fixation with Screw Plates," *Clinical Orthopaedics and Related Research*, No. 203 (Feb. 1986), pp. 18-33.
Berry, James L. et al., "A Morphometric Study of Human Lumbar and Selected Thoracic Vertebrae," *Spine*, vol. 12, No. 4 (1987), pp. 362-367.
Roy-Camille, R. et al., "Posterior Spinal Fixation with Transpedicular Screws and Plates," Groupe Hospitalier, Paris, France.

*Primary Examiner*—David J. Isabella
*Assistant Examiner*—Elizabeth M. Burke
*Attorney, Agent, or Firm*—Christensen, O'Connor, Johnson & Kindness

[57] ABSTRACT

A sacral implant system includes first and second sacral plates that are affixed on opposite sides of the sacrum adjacent the lumbosacral junction. Pedicle, lateral and oblique mounting means are provided for rigidly affixing the sacral plates to the sacrum. First and second fixation rods extend in a superior direction along the lumbar portion of the spine. One or more connecting members tie the rods together. The superior most vertebra to be fixed is tied to the implant system with a special offset fixation plate and pedicle screw. Conventional vertebra hooks can also be used as necessary. Intermediate vertebra are tied to the system with a straight fixation plate and pedicle screw.

27 Claims, 5 Drawing Sheets

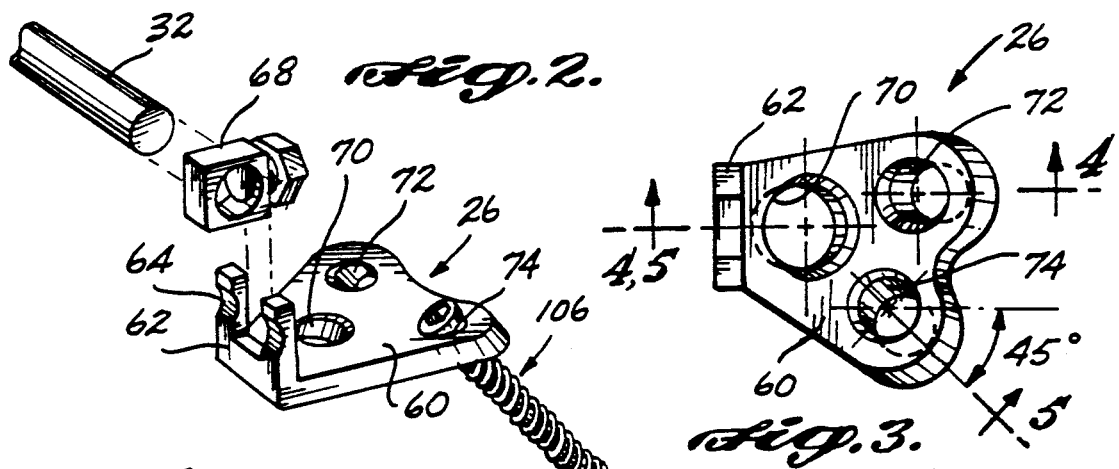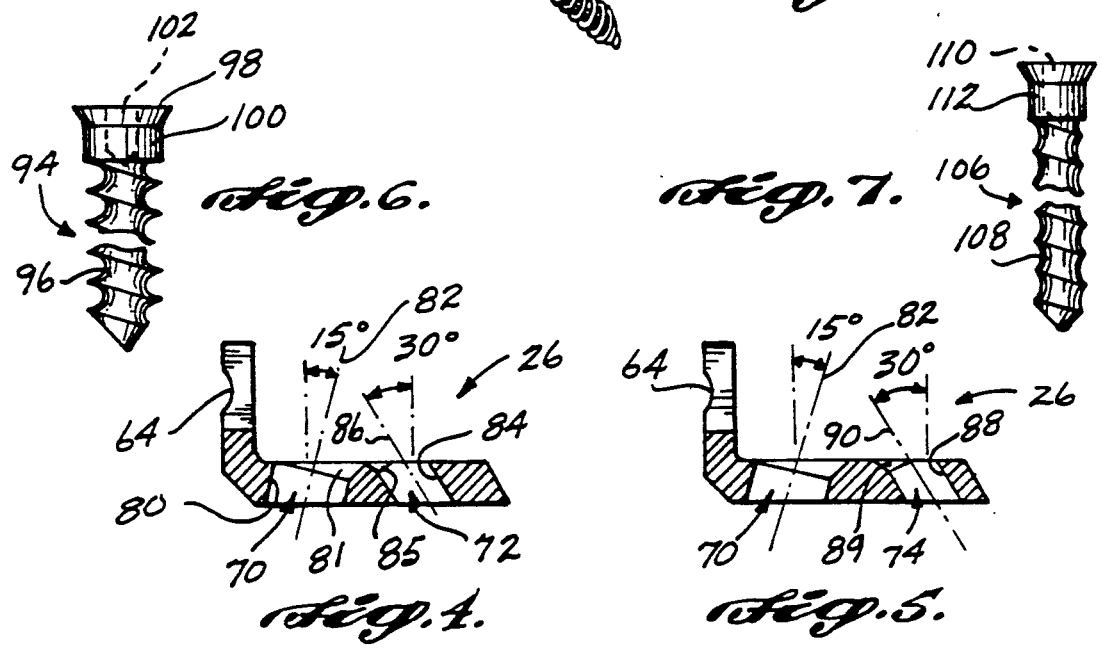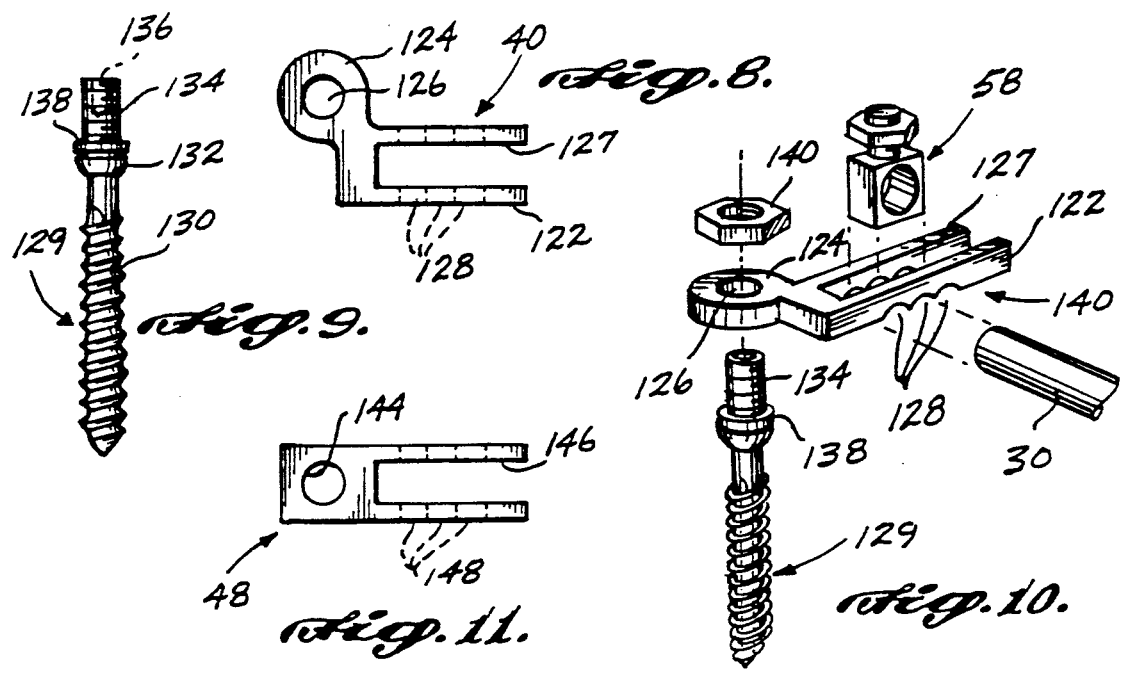

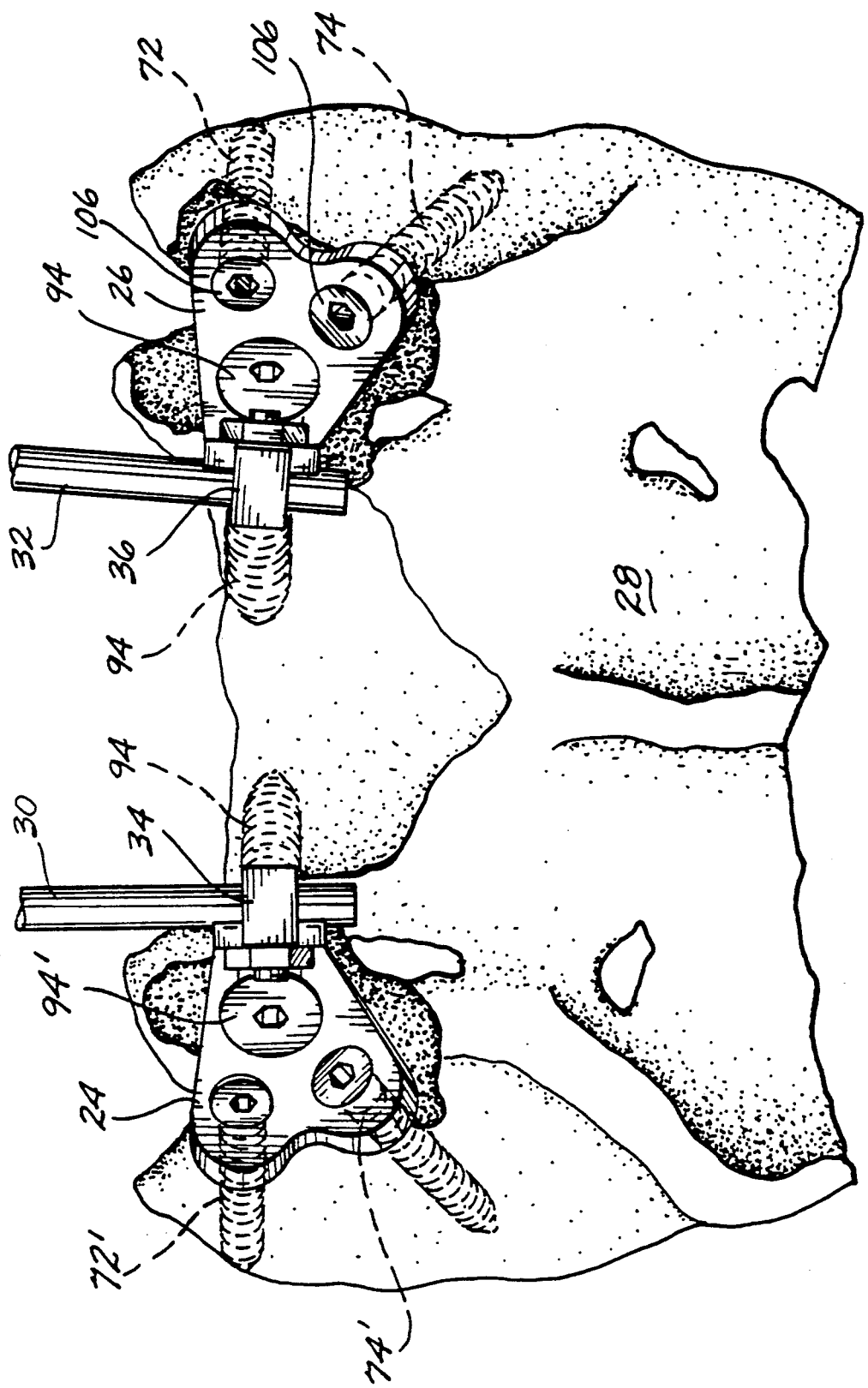

SACRAL IMPLANT SYSTEM

BACKGROUND OF THE INVENTION

The present invention relates to sacral implants, and more particularly to an improved implant system for fixing a stabilizing appliance to the sacrum and to the lumbar vertebrae.

Spinal fusion, especially in the lumbar and sacral region is regularly employed to correct and stabilize spinal curves, to prevent recurrence of spinal curves and to stabilize weakness in trunks that result from degenerative discs and joint disease, deficient posterior elements, spinal fracture, and other debilitating problems. Spinal implant systems have been used regularly to stabilize the lumbar and sacral spine temporarily while solid spinal fusions develop.

Several temporary stabilization systems are currently in use. All perform adequately, however leave room for improvement. For example, an implant system for attaching the superior most lumbar vertebra (L1) to the implant without interfering with normal motion of the next superior vertebra needs to be developed. Additionally, implant systems that achieve stronger sacral fixation, easier use for multiple segment fixation, and easier use with spinal deformity are needed. Further, better implant systems for rigidly tying the base of the system to the sacrum must be developed.

SUMMARY OF THE INVENTION

The present invention provides a sacral implant system that rigidly affixes the base of the implant system to the sacrum while allowing ease of installation and flexibility of design. Moreover, the present system provides apparatus for securing the upper portion of the implant system to, for example, the L-1 vertebra, without interfering with the next superior most vertebra (T-2) and any or all vertebrae in between. The sacral implant system of the present invention comprises first and second sacral plates for mounting on opposite sides of the sacrum adjacent the lumboscral junction. Each of the sacral plates have pedicle, lateral, and oblique mounting means for rigidly affixing each of the sacral plates to the sacrum. The system also includes first and second rods extending in a superior direction and generally parallel relationship from respective ones of the sacral plates. The rods are situated on opposite sides of the sagittal plane. Means are also provided for rigidly affixing the rods to respective sacral plates. At least one crosslink plate is employed to rigidly interconnect the rods at a location superior to the sacral plates. Finally, a superior fixation plate having a lateral portion and a medial portion is employed to affix the superior most vertebra to be fused to the implant system. A pedicle screw is fixed to and through the pedicle of the vertebra. The lateral portion of the fixation plate is rigidly affixed to the pedicle screw. The medial portion of the fixation plate is offset in an inferior direction sufficiently far so that it avoids the inferior articulate process of the next superior vertebra. In this manner the next superior vertebra can moved in a normal fashion relative to the vertebra to be fused during the temporary stabilization. Preferably, a lateral fixation plate is also used for pedicle fixation of intermediate vertebrae.

In another aspect of the invention, a specialized pedicle screw is provided for attachment of the offset and lateral fixation plates to the vertebra. The screw includes a first threaded portion for threading into the vertebra, a subhead portion and a second threaded portion projecting above the subhead. The second threaded portion is adapted to receive a nut. The subhead has a diameter greater than the second threaded portion and an upwardly facing shoulder lying in a plane substantially orthogonal to the axis of the screw. In use, the shoulder engages the anterior surface of the fixation plate while the nut is threaded on the second threaded portion and bears down against the posterior surface of the plate to secure the plate and screw together.

BRIEF DESCRIPTION OF THE DRAWINGS

A better understanding of the present invention can be derived by reading the ensuing specification in conjunction with the accompanying drawings wherein:

FIG. 2 is an isometric view of a right lateral sacral plate constructed in accordance with the present invention;

FIG. 3 is a plan view (in the dorsal plane) of a sacral plate shown in FIG. 2;

FIG. 4 is a cross-sectional view taken along section line 4—4 of FIG. 3;

FIG. 5 is a cross-sectional line taken along broken cross-sectional line 5—5 of FIG. 3;

FIG. 6 and FIG. 7 are elevation views of fixation screws for use with the sacral plate;

FIG. 8 is a plan view of the offset fixation plate that is constructed in accordance with the present invention;

FIG. 9 is a elevation view of a pedicle screw for use with the fixation plate of FIG. 8;

FIG. 10 is an exploded isometric view of the fixation plate and screw of FIG. 9 shown in conjunction with a fixation rod and fastening system used in accordance with the present invention;

FIG. 11 is a plan view of a straight fixation plate;

FIG. 12 is an enlarged dorsal view of a superior portion of the sacrum showing the sacral plates implanted in accordance with the present invention;

DETAILED DESCRIPTION OF THE INVENTION

Figure 1:
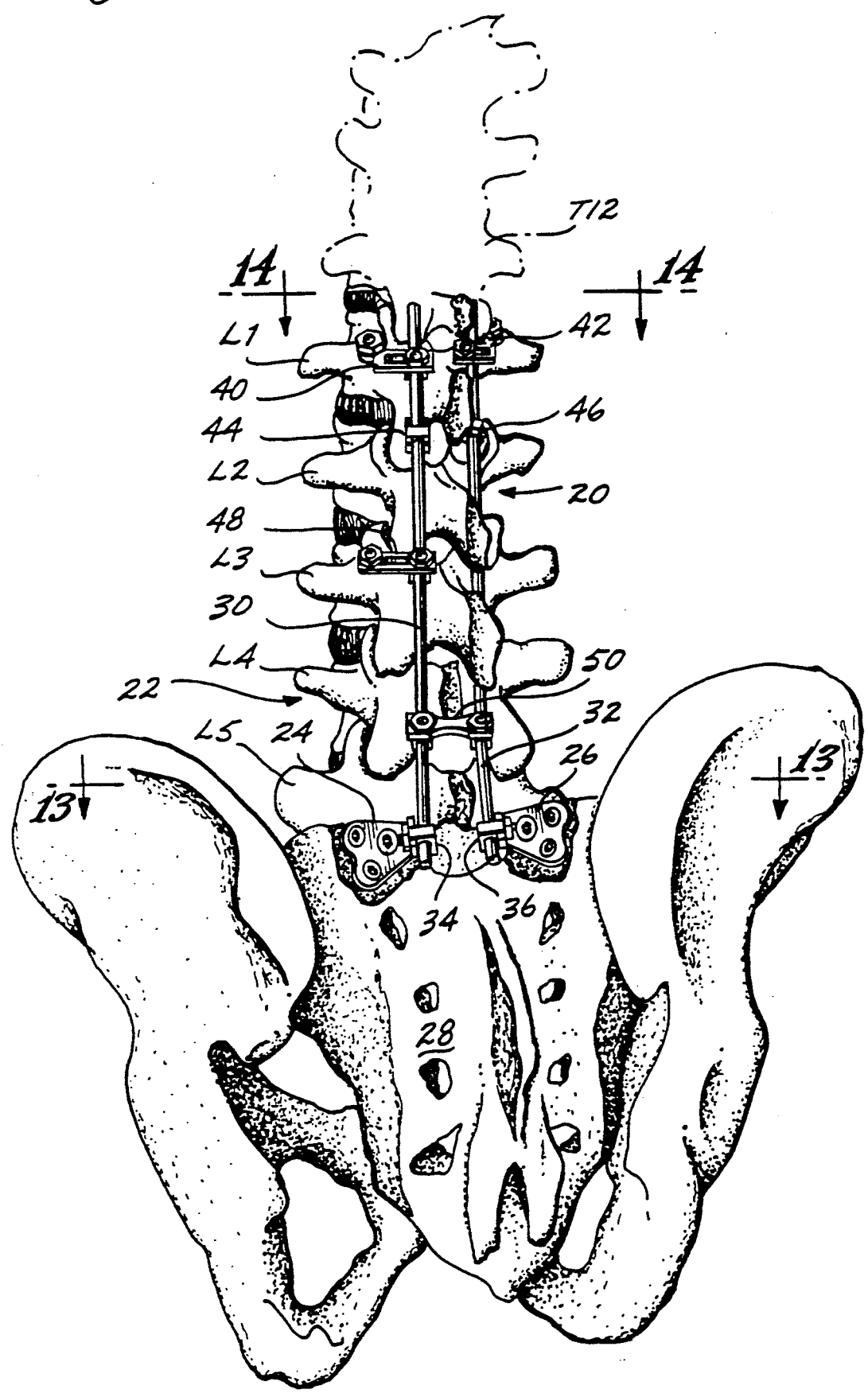
FIG. 1 is an isometric view of the spinal implant system of the present invention as applied to the lumbar spine.

Referring first to FIG. 1, the spinal implant system 20 constructed in accordance with the present invention is affixed to the lumbar spine, generally designated 22. The implant system includes a pair of sacral plates 24 and 26 affixed to the sacrum 28 adjacent the lumboscaral joint. A pair of fixation rods 30 and 32 extend in a superior direction on opposite sides of the sagittal plane from the sacral plates posterior to the lumbar vertebrae L5, L4, L3, L2 and L1. Rods 30 and 32 terminate adjacent the superior portion of vertebra L1. Conventional fasteners 34 and 36 securely affix the rods 30 and 32 respectively to the sacral plates 24 and 26.

At the superior end of the rods, a pair of offset fixation plates 40 and 42 affix the upper ends of the rods to the L1 vertebra. Inferior to that location, a pair of conventional inferior hooks 44 and 46 grasp the inferior portion of the L1 vertebra to secure it relative to the rods 30 and 32. At intermediate locations a straight fixation plate 48 is employed to affix vertebra L3 to the rods 30 and 32. Immediately superior to the sacral plates a connecting member 50 rigidifies the rods 30 and 32 relative to each other. One of ordinary skill in this technique will readily recognize that one or more connecting members 50, straight fixation plates 48, and hooks 44 can be employed as needed.

The implant system 20 constructed and employed in accordance with the present invention provides a rigid stabilization system for the lumbar spine. The system rigidly ties the sacrum to one or more of the lumbar vertebrae. Moreover the offset fixation plates 40 and 42 allow the upper portion of the implant system to be rigidly affixed to the superior lumbar vertebra L1 while avoiding contact with the inferior processes of the next superior vertebra T12. In this manner the T12 vertebra can move in a normal manner while stabilization of the lumbar spine occurs.

Referring now to FIGS. 2, 3, 4 and 5, the right sacral plate is illustrated. The right sacral plate is a mirror image of the left sacral plate, therefore, only the right plate will be described in detail. The right sacral plate 26 has a base 60 having a posterior surface and an anterior surface. The anterior surface of the plate is designed to intimately contact the posterior surface of the sacrum adjacent the lumbosacral joint. In position, the base 60 lies generally in a plane generally tangential to the portion of the sacrum adjacent the lumbosacral joint. For purposes of this description, that plane will be referred to as the sacral or dorsal plane.

A U-shaped flange 62 extends posteriorly from the medial portion of the base 60. The medial surface of the flange 62 carries a groove 64 oriented in a superior/inferior direction for receiving a fixation rod 32. A conventional rod clamp 68 is employed to securely and rigidly affix the rod 66 in the groove 64 on the flange 62. The lateral portion of the sacral plate 26 carries three bores that extend from the posterior surface of the base 60 in a generally anterior direction. These bores are the pedicle bore 70, the lateral bore 72 and the oblique bore 74. The bores 70, 72 and 74, while extending in an anterior direction, are not orthogonal to the sacral plane.

Instead, the pedicle bore 70 has a cylindrical section 80 having an axis 82 extending in an anterior and medial direction that is offset in the medial direction preferably at an angle of 15 degrees to a line orthogonal to the sacral plane. A countersink bore 81 is located posterior to the cylindrical section 80 and emerges onto the posterior surface of the sacral plate. This angle can be varied from 0 degrees to 20 degrees, depending upon the particular sacral anatomy being extends fixed. However, it is understood that the screw that extends through this opening extends through the pedicle of the sacrum and must always lie within the pedicle. It has been found that 15 degrees is the angle most universally acceptable for this orientation. In the present embodiment, the axis 82 is not inclined in a superior or inferior direction relative to a plane perpendicular to the sacral plate. It however can be inclined superiorly so that the vertebral end plate, rather than the anterior cortex, can be engaged by the end of the screw.

The lateral bore 72 has a cylindrical section 84 having an axis 86 extending in an anterior and lateral direction that is preferably offset in the lateral direction at an angle of 30 degrees from a line orthogonal to the sacral plane. If desired, one of ordinary skill may also vary the lateral angle from 30 degrees up to 45 degrees. Preferably the axis 86 is not canted in either an inferior or superior direction relative to the sacral plate. However, depending upon the sacral anatomy, the axis can be canted from 0 degrees to 15 degrees in the superior direction when viewed in the sacral plane. A countersink bore 85 is located posterior to the cylindrical section 85 and emerges onto the posterior surface of the sacral plate.

The oblique bore 74 also has a cylindrical section 88 having an axis 90 having two offsets in the lateral and inferior directions. The axis 90 when viewed in the sacral plane is first preferably offset 45 degrees from a lateral line, but may be varied from 30 degrees to 60 degrees. Secondly, the axis 90 is offset in the lateral direction preferably 30 degrees from a line orthogonal to the sacral plane but again may be varied from 30 degrees to 45 degrees. A countersink 89 is located posterior to the cylindrical section 88 and also emerges onto the posterior surface of the sacral plate.

Referring now to FIG. 6, the pedicle screw 94 employed with the sacral plate has a unique construction. It has a lower threaded portion 96, an upper flared head 98 and a cylindrical section 100 immediately below the head 98. The head also carries an allen socket 102 so that the screw can be rotated into a hole drilled in the pedicle. The bone engaging threads on the lower threaded portion 96 are of conventional design. The cylindrical section 100 has a diameter slightly less than the diameter of the cylindrical section 80 of pedicle bore 70. The diameters are chosen such that when the cylindrical section 100 is in the cylindrical section 80, the screw 94 can rotate and reciprocate. However, the tolerances are such that the screw cannot angulate or toggle relative to the axis 82. The upper flared portion 98 is configured to mate with countersink 81 when the screw is completely threaded into the sacrum.

Referring to FIG. 7, the same screw 106 is employed in both the lateral bore 72 and the oblique bore 74. Screw 106 also has a lower threaded portion 108, a flared head 110 and a cylindrical section 112. Cylindrical section 112 is sized relative to the cylindrical sections 84 and 88 to allow rotation and reciprocation but not angulation. The flared head 110 is configured to mate with the countersinks 85 and 89 when the screws are completely threaded into the sacrum.

Referring now to FIGS. 8 and 10, the offset fixation plate 40 includes a medial portion 122 and a lateral portion 124. The fixation plate of FIG. 8 is employed on the left side of the fixation system. A similar fixation plate, having the mirror image of plate 40, is employed on the right side; however, it is not shown in the drawings. The lateral portion 124 carries a bore 126 that extends in a posterior/anterior direction when installed. The medial portion 122 is offset in an inferior direction from the lateral portion. 124. The medial portion 122 carries a lateral slot 127. The anterior surface of the medial portion 122 carries a plurality of grooves 128 that extend in an inferior/superior direction and intersect the slot 127. These grooves have a diameter equivalent to the fixation rod 30. A conventional rod to clamp fastener 58 is employed to secure the fixation plate 40 to the fixation rod 30.

A special pedicle screw 129 is employed with the offset fixation plate. Referring to FIG. 9, the pedicle screw includes a lower threaded portion 130, a subhead portion 132 and an upper threaded portion 134. The upper threaded portion 134 has an allen socket 136 extending axially into its upper end. The subhead has a diameter larger than the upper threaded portion 134 and terminates in its upward end in a shoulder 138 that is positioned in a plane orthogonal to the axis of the screw 129. Referring now to FIG. 10, the pedicle screw is received by the bore 126, which is sized just slightly larger than the upper threaded portion 134 so that the pedicle screw can reciprocate relative to the offset fixation plate 40, but cannot angulate relative to the screw axis when engaging the bore 126. A conventional nut 140 is threaded onto the upper portion 134 of the pedicle screw 129 securing the shoulder 138 against the anterior surface of the fixation plate while the nut 140 snugs against the posterior surface, thus rigidly interlocking the pedicle screw 129 and the fixation plate.

A straight fixation plate 48 is illustrated in FIG. 11. The straight fixation plate is similar in construction to the offset fixation plate 40 except that it does not contain the offset. It carries a similar bore 144 for receiving a pedicle screw similar to screw 129, a lateral slot 146 and rod engaging grooves 148 for securing the plate 48 to a fixation rod.

Figure 13:
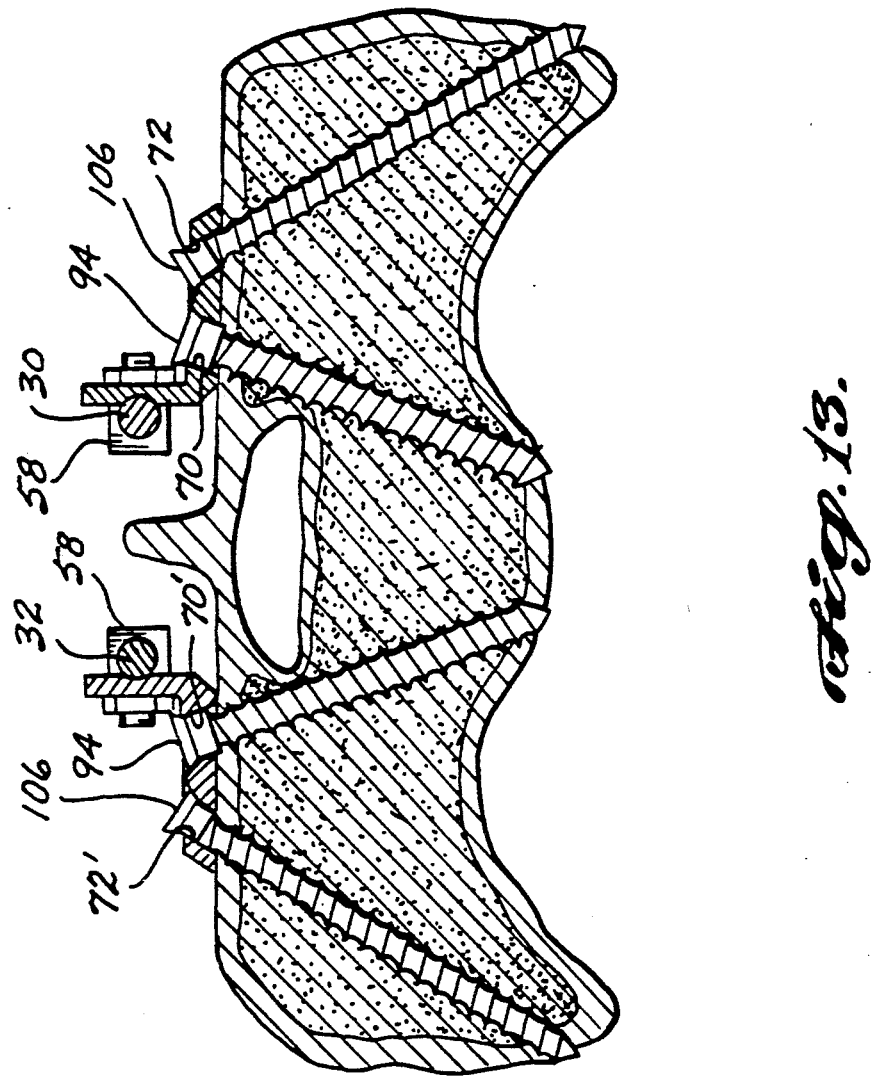
FIG. 13 is an enlarged cross-sectional view taken along section line 13—13 of FIG. 1 through the sacrum looking in an inferior direction at the sacral implant system of the present invention.

Referring to FIGS. 12 and 13, in use the sacral plates 24 and 26 are affixed to the sacrum 28 adjacent the lumboscral junction. As desired and as necessary, the anterior surface of the sacrum can be smoothed so as to receive the anterior surface of the sacral plates 24 and 26 in snug relationship. The pedicle screws 94 and 94', for use in the pedicle bores of the sacral plates, is threaded into appropriate bores made by the surgeon through the pedicle of the sacrum. The pedicle screws are snugged down so that the flared heads are seated firmly in the countersinks in the respective plates. A torque ranging from 6 to 10 in/lb. can be used to snug the screws. The physician also makes appropriate bores into the sacrum that are aligned with the lateral bores 72 and 72' and with the oblique bores 74 and 74'. Screws 106 are inserted through the lateral and oblique bores 72 and 74 in the right plate, and bores 72' and 74' in the left plate. All the screws 106 are snugged down so that the flared heads seat snugly in the countersinks in the anterior surface of the sacral plates. Again a torque of 6 to 10 in/lb. is appropriate for snugging the screws into the plate.

In this manner, the three screws in each sacral plate all diverge from each other. As a result, the screws cannot be easily pulled from the bores in the bone. A force in the direction of the axis of one of the screws will be partially distributed over the bone on which the remaining two screws bear. In this manner, full force cannot be exerted in the direction of the axis of a single screw and thus a single screw cannot be sheared from its bore in an easy manner. This construction provides significant advantages over the prior art while allowing independent placement of a sacral plate on each side of the sacrum. For example, screw placement is designed to achieve fixation in the proximal part of the sacrum, which has the strongest bone. The oblique screw is designed to be proximal to and parallel the S1 foramin, thereby avoiding damage to the S1 nerve. The medial screw is inclined medially to allow bicortical fixation while avoiding neurovascular structures directly anterior to the S1 pedicle. The lateral screw is also designed to allow bicortical fixation lateral to the significant neurovascular strucutures.

Figure 14:
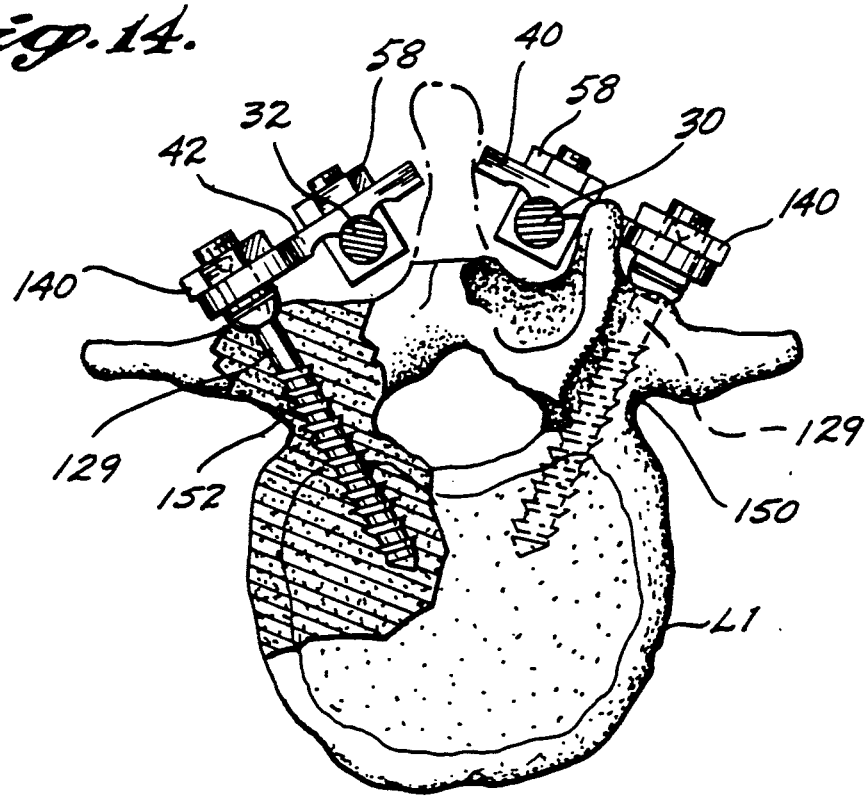
FIG. 14 is an enlarged cross-sectional view taken along section line 14—14 of FIG. 1 of the pedicle screw and offset fixation plate implanted in accordance with the present invention looking in an inferior direction.
Figure 15:
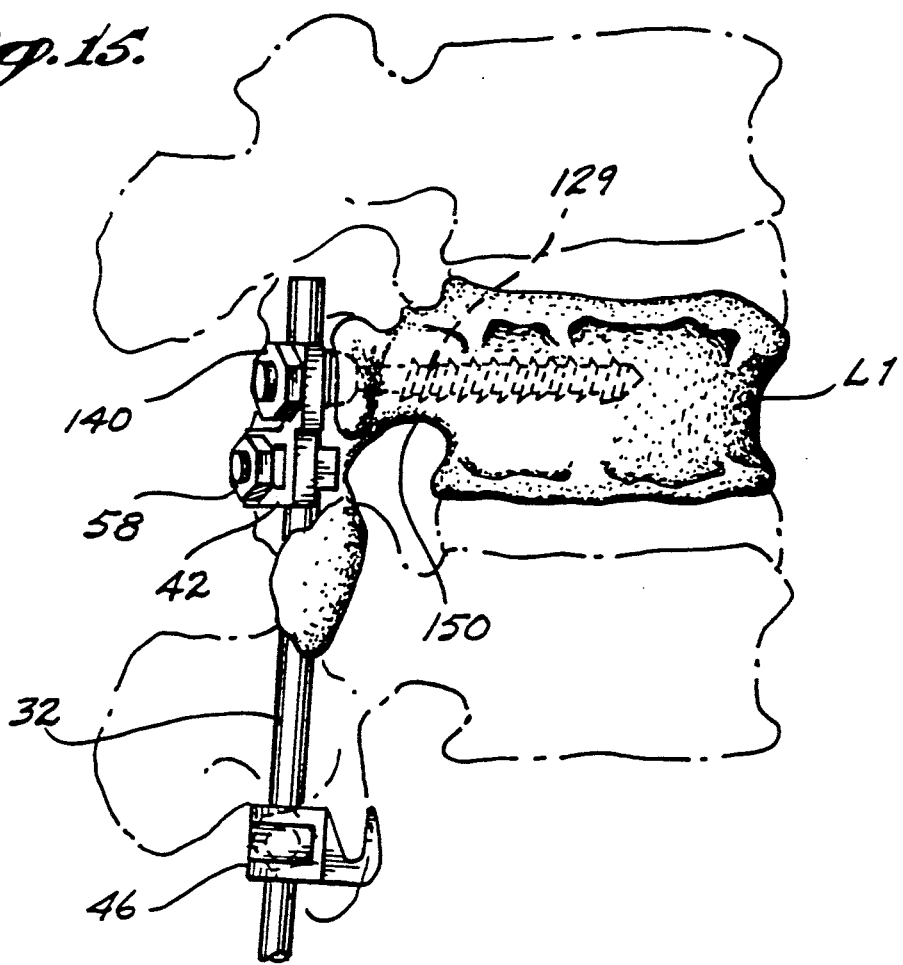
FIG. 15 is a lateral view looking from right to left of the offset fixation plate shown in FIG. 14.

Referring now to FIGS. 14 and 15, offset fixation plates 40 and 42 are shown affixed by conventional fasteners 58 to fixation rods 30 and 32 The pedicle screws 129 are threaded into suitable bores in the left and right pedicle 150 and 152 of the L1 vertebra. Nuts 140 are threaded onto the upper portions of the pedicle screws 129 and tightened against the anterior surfaces of the fixation plates 40. The fasteners 58 thereafter are tightened to secure the other end of the plate to the fixation rods 30 and 32. In this manner, the upper end of the lumbar spine implant system can be secured to the L1 vertebra without interfering with the next superior vertebra.

The present invention has been described in connection with the preferred embodiment. One of ordinary sill will be able to effect various alterations, substitutions of equivalents and other changes without departing from the broad concepts imparted herein. It is, therefore, intended that the letters patent issued hereon be limited only by the definition contained in the appended claims and equivalents thereof.

The embodiments of the invention in which an exclusive property or privilege is claimed are defined as follows:

1. A sacral implant system comprising:
   first and second discrete sacral plates for mounting on opposite sides of said sacrum adjacent the lumbosacral junction, each of said sacral plates having pedicle, lateral and oblique mounting means for rigidly fixing each of said sacral plates independently to opposite lateral portions of said sacrum,
   first and second rods extending in a superior direction in a generally parallel relationship from respective ones of said sacral plates on opposite sides of the centerline of said lumbar spine, and means rigidly fixing said rods to said sacral plates,
   at least connecting member rigidly interconnecting said rods superior to said sacral plates, and
   a superior offset fixation plate rigidly affixed to at least one of said rods, a pedicle screw fixed to and through the pedicle of a vertebra, and means rigidly affixing said pedicle screw to said offset fixation plate,
   each of said pedicle, lateral and oblique mounting means including a fixation screw having a lower threaded portion, a head and a cylindrical section adjacent said head, said sacral plate including cylindrical bores corresponding to each of said pedicle, lateral and oblique mounting means, each of said bores having a diameter slightly greater than a respective cylindrical section on a respective fixation screw enabling said screw to rotate and reciprocate in said bore while substantially eliminating angular movement of said screw relative to said plate, said cylindrical bore of said pedicle mounting means having an axis that extends in a medial and anterior direction from said sacral plate, said cylindrical bore of said pedicle mounting means being located medially from the cylindrical bores of said lateral and oblique mounting means.

2. The system of claim 1 wherein said axis offset in the medial direction at an angle ranging from 0 to 20 degrees relative to a line orthogonal to the sacral plane.

3. The system of claim 1 wherein the axis is oriented an an angle of about 15 degrees relative to a line orthogonal to the sacral plane.

4. The system of claim 1 wherein the cylindrical bore of said lateral mounting means has an axis extending in a lateral and anterior direction relative to said sacral plate.

5. A sacral plate for use in a sacral implant system comprising:
 a plate having a posterior surface and an anterior surface, said anterior surface being configured to the positioned against the posterior surface of the sacrum adjacent the lumbosacral junction, said sacral plate having means for attaching to a fixation rod, said sacral plate also having a pedicle, lateral and oblique mounting means for rigidly fixing said sacral plate to said sacrum at a location lateral from the sagittal plane, each of said pedicle, lateral and oblique mounting means including a cylindrical bore, of said pedicle mounting means having an axis that extends in a medial and anterior direction relative to the sacral plane, the cylindrical bore of said pedicle mounting means being positioned medially relative to the cylindrical bores of said lateral and oblique mounting means.

6. The plate of claim 5 wherein said axis if offset in the medial direction at an angle of about 0 degrees to 20 degrees relative to a line orthogonal to the sacral plane.

7. The plate of claim 1 wherein said axis is oriented at an angle of about 15 degrees relative to a line orthogonal to the sacral plane.

8. The plate of claim 5 wherein the cylindrical bore of said lateral mounting means has an axis extending in a lateral and anterior direction relative to said sacral plane.

9. The plate of claim 8 wherein said axis if offset in the lateral direction at an angle of about 30 degrees to about 45 degrees relative to a line orthogonal to said sacral plane.

10. The plate of claim 9 wherein said axis is oriented at an angle of about 30 degrees relative to a line orthogonal to the sacral plane.

11. The plate of claim 5 wherein the cylindrical bore of said oblique mounting means has an axis extending in a lateral, anterior and inferior direction relative to said sacral plane.

12. The plate of claim 11 wherein said axis when viewed in the sacral plane, is offset in the inferior direction at an angle of about 30 degrees to about 60 degrees relative to a lateral line in said sacral plane and is offset in the lateral direction from about 30 degrees to about 45 degrees relative to a line orthogonal to said sacral plane.

13. The plate of claim 12 wherein said axis is offset inferiorly at an angle of about 45 degrees relative to a lateral line in the sacral plane and is offset laterally at an angle of about 30 degrees relative to a line orthogonal to the sacral plane.

14. A sacral implant system comprising:
 first and second sacral plates mounting on opposite sides of said sacrum adjacent the lumbosacral junction, each of said sacral plates having pedicle, lateral and oblique mounting means for rigidly fixing each of said sacral plates to opposite lateral portions of said sacrum,
 first and second rods extending in a superior direction in a generally parallel relationship from respective ones of said sacral plates on opposite sides of the centerline of said lumbar spine, and means rigidly fixing said rods to said sacral plates,
 at least one connecting member rigidly interconnecting said rods superior to said sacral plates, a superior offset fixation plate rigidly affixed to at least one of said rods, a pedicle screw fixed to and through the pedicle of a vertebra, and means rigidly affixing said pedicle screw to said offset fixation plate, said offset fixation plate having a medial portion and an integral lateral portion offset in the superior direction, the medial portion being positioned below the interior processes of the next superior vertebra relative to the vertebra to be fixed, the offset portion being positionable over the pedicle of the vertebra to be fixed.

15. The system of claim 14 wherein the medial portion of said offset plate has a lateral slot, the anterior side thereof having a plurality of slots oriented in the superior/inferior direction for receiving said rod at a plurality of lateral distances from an adjacent pedicle fixation screw.

16. A sacral implant system comprising:
 first and second sacral plates for mounting on opposite sides of said sacrum adjacent the lumbosacral junction, each of said sacral plates having pedicle, lateral and oblique mounting means for rigidly fixing each of said sacral plates to opposite lateral portions of said sacrum,
 first and second rods extending in a superior direction in a generally parallel relationship from respective ones of said sacral plates on opposite sides of the centerline of said lumbar spine, and means rigidly fixing said rods to said sacral plates,
 at least one connecting member rigidly interconnecting said rods superior to said sacral plates, a superior offset fixation plate rigidly affixed to at least one of said rods, a pedicle screw fixed to and through the pedicle of a vertebra, and means rigidly affixing said pedicle screw to said offset fixation plate, and
 a straight fixation plate for fixing an intermediate vertebra to one of said rods, said straight fixation plate having a medial portion and an integral lateral portion, said lateral portion including an aperture for receiving a pedicle fixation screw, said medial portion having a plurality of slots on its anterior side oriented in a superior/inferior direction for receiving a rod at plurality of lateral distances from an adjacent pedicle fixation screw.

17. A sacral implant system comprising:
 first and second sacral plates for mounting on opposite sides of said sacrum adjacent the lumbosacral junction, each of said sacral plates having means for attaching to a fixation rod, each of said sacral plates also having pedicle, lateral and oblique mounting means for rigidly fixing each of said sacral plates to opposite lateral portions of said sacrum, each of said pedicle, lateral and oblique mounting means including a fixation screw having a lower threaded portion, a head and a cylindrical section adjacent said head, said sacral plate including cylindrical bores corresponding to each of said pedicle, lateral and oblique mounting means, each of said bores having a diameter slightly greater than a respective cylindrical section on a fixation screw enabling said screw to rotate and reciprocate in said bore while substantially eliminating angular movement of said screw relative to said plate, said cylindrical bore of said lateral mounting means having an axis extending in a lateral and anterior direction relative to said sacral plate, said axis of said cylindrical bore being offset in the lateral direction at an angle of from 30 degrees to 45 degrees relative to a line orthogonal to the sacral plane.

18. The system of claim 17 wherein said axis of said cylindrical bore is oriented at an angle of about 30 degrees relative to a line orthogonal to the sacral plane.

19. A sacral implant system comprising:

first and second sacral plates for mounting on opposite sides of said sacrum adjacent the lumbosacral junction, each of said sacral plates having means for attaching to a fixation rod, each of said sacral plates also having pedicle, lateral and oblique mounting means for rigidly fixing each of said sacral plates to opposite lateral portions of said sacrum, each of said pedicle, lateral and oblique mounting means including a fixation screw having a lower threaded portion, a head and a cylindrical section adjacent said head, said sacral plate including cylindrical bores corresponding to each of said pedicle, lateral and oblique mounting means, each of said bores having a diameter slightly greater than a respective cylindrical section on a fixation screw enabling said screw to rotate and reciprocate in said bore while substantially eliminating angular movement of said screw relative to said plate, said cylindrical bore of said oblique mounting means having an axis extending in a medial, anterior, and inferior direction relative to said sacral plate, said axis of said cylindrical bore when viewed in the sacral plane being offset in the inferior direction at an angle of about 30 degrees to about 60 degrees relative to a lateral line in the sacral plane and being offset in the lateral direction at an angle of about 30 degrees to about 45 degrees relative to a line orthogonal to the sacral plane.

20. The system of claim 19 wherein said axis of said cylindrical bore is offset inferiorly at an angle of about 45 degrees relative to a lateral line in the sacral plane and is offset laterally at an angle of about 30 degrees relative to a line orthogonal to the sacral plane.

21. A sacral plate for use in a sacral implant system comprising:

a plate having a posterior surface and an anterior surface, said anterior surface being configured to be positioned against the posterior surface of the sacrum adjacent the lumbosacral junction, said sacral plate having means for attaching to a fixation rod, said sacral plate also having a pedicle, lateral and oblique mounting means for rigidly fixing said sacral plate to said sacrum at a location lateral from the sagittal plane, each of said pedicle, lateral and oblique mounting means including a fixation screw having a lower threaded portion, a head, and a cylindrical section intermediate said head and said threaded portion, said plate including cylindrical bores corresponding to each of said pedicle, lateral and oblique mounting means, each of said bores having a diameter slightly greater than a respective cylindrical section enabling said cylindrical section to rotate and reciprocate in said bore while substantially eliminating angular movement of said screw relative to said plate, the cylindrical bore of said lateral mounting means having an axis extending in a lateral and anterior direction relative to said sacral plane, said axis being offset in the lateral direction at an angle of from about 30 degrees to about 45 degrees relative to a line orthogonal to said sacral plane.

22. The plate of claim 21 wherein said axis is oriented at angle of about 30 degrees relative to a line orthogonal to the sacral plane.

23. A sacral plate for use in a sacral implant system comprising:

a plate having a posterior surface and an anterior surface, said anterior surface being configured to be positioned against the posterior surface of the sacrum adjacent the lumbosacral junction, said sacral plate having means for attaching to a fixation rod, said sacral plate also having a pedicle, lateral and oblique mounting means for rigidly fixing said sacral plate to said sacrum at a location lateral from the sagittal plane, each of said pedicle, lateral and oblique mounting means including a fixation screw having a lower threaded portion, a head, and a cylindrical section intermediate said head and said threaded portion, said plate including cylindrical bores corresponding to each of said pedicle, lateral and oblique mounting means, each of said bores having a diameter slightly greater than a respective cylindrical section enabling said cylindrical section to rotate and reciprocate in said bore while substantially eliminating angular movement of said screw relative to said plate, said cylindrical bore of said oblique mounting means having an axis extending in a medial, anterior, and inferior direction relative to said sacral plate, said axis when viewed in the sacral plane being offset in the inferior direction at an angle of about 30 degrees to about 60 degrees relative to a lateral line in said sacral plane and is offset in the lateral direction from about 30 degrees to about 45 degrees relative to a line orthogonal to said sacral plane.

24. The plate of claim 23 wherein said axis if offset inferiorly at an angle of about 45 degrees relative to a lateral line in the sacral plane and is offset laterally at an angle of about 30 degrees relative to a line orthogonal to the sacral plane.

25. A sacral implant system comprising:

first and second sacral plates for mounting on opposite sides of said sacrum adjacent the lumbosacral junction, each of said sacral plates having pedicle, lateral and oblique mounting means for rigidly fixing each of said sacral plates to opposite lateral portions of said sacrum, first and second rods extending in a superior direction in a generally relationship from respective ones of said sacral plates on opposite sides of the centerline of said lumbar spine, and means rigidly fixing said rods to said sacral plates, a least one connecting member rigidly interconnecting said rods superior to said sacral plates, a superior offset fixation plate rigidly affixed to at least one of said roods, a pedicle screw fixed to and through the pedicle of a vertebra, and means rigidly affixing said pedicle screw to said offset fixation plate, said offset fixation plate having a medial portion and an integral lateral portion offset in the superior direction, the medial portion being positioned below the inferior processes of the next superior vertebra relative to the vertebra to be fixed, the offset portion being positionable over the pedicle of the vertebra to be fixed.

26. The system of claim 25 wherein the medial portion of said offset plate has a lateral slot, the anterior side thereof having a plurality of slots oriented in the superior/inferior deviation of receiving said rod at a plurality of lateral distances from an adjacent pedicle fixation screw.

27. A sacral implant system comprising:
   first and second sacral plates for mounting on opposite sides of said sacrum adjacent the lumbosacral junction, each of said sacral plates having pedicle, lateral and oblique mounting means for rigidly fixing each of said sacral plates to opposite lateral portions of said sacrum,
   first and second rods extending in a superior direction in a generally parallel relationship from respective ones of said sacral plates on opposite sides of the centerline of said lumbar spine, and means rigidly fixing said rods to said sacral plates,
   at least one connecting member rigidly interconnecting said rods superior to said sacral plates,
   a superior offset fixation plate rigidly affixed to at least one of said rods, a pedicle screw fixed to and through the pedicle of a vertebra, and means rigidly affixing said pedicle screw to said offset fixation plate, and
   a straight fixation plate for fixing an intermediate vertebra to one of said rods, said straight fixation plating having a medial portion and an integral lateral portion, said lateral portion including an aperture for receiving a pedicle fixation screw, said medial portion having a plurality of slots on its anterior side oriented in a superior/inferior direction for receiving a rod at a plurality of lateral distances from an adjacent pedicle fixation screw.

* * * * *

UNITED STATES PATENT AND TRADEMARK OFFICE
CERTIFICATE OF CORRECTION

PATENT NO. : 5,127,912　　　　　　　　　　　　　　　Page 1 of 2

DATED : July 7, 1992

INVENTOR(S) : R.C. Ray et al.

It is certified that error appears in the above-identified patent and that said Letters Patent is hereby corrected as shown below:

COLUMN　　LINE

| COLUMN | LINE | |
|---|---|---|
| [56] Other Publications | | "Lumber" should read --Lumbar-- |
| 1 | 14 | "debiliating" should read --debilitating-- |
| 1 | 37 | "(T-2)" should read --(T-12)-- |
| 2 | 61 & 62 | "lumbosca-ral" should read --lumbosacral-- |
| 3 | 8 | "plates" should read --plates,-- |
| 3 | 18 | "Moreover" should read --Moreover,-- |
| 3 | 58 | after "being" delete "extends" |
| 4 | 61 | "portion. 124." should read --portion 124.-- |
| 5 | 10 | after "screw" insert --129-- |
| 5 | 30 | "lumboscral" should read --lumbosacral-- |
| 6 | 2 | "strucutures" should read --structures-- |
| 6 | 5 | "32" should read --32.-- |
| 6 | 18 | "sill" should read --skill-- |
| 6 | 39 | after "least" insert --one-- |
| 6 | 67 | "an" (first occurrence) should read --at-- |
| 7 | 9 | "the positioned" should read --be positioned-- |

UNITED STATES PATENT AND TRADEMARK OFFICE
CERTIFICATE OF CORRECTION

PATENT NO. : 5,127,912

DATED : July 7, 1992

INVENTOR(S) : R.C. Ray et al.

It is certified that error appears in the above-identified patent and that said Letters Patent is hereby corrected as shown below:

| COLUMN | LINE | |
|---|---|---|
| 7 | 17 | after "bore," insert --the cylinder bore-- |
| 7 | 23 | "if" should read --is-- |
| 7 | 26 | "claim 1" should read --claim 6-- |
| 7 | 33 | "if" should read --is-- |
| 8 | 46 | after "at" insert --a-- |
| 10 | 4 | "at angle" should read --at an angle-- |
| 10 | 50 | after "generally" insert --parallel-- |
| 10 | 57 | "roods" should read --rods-- |
| 11 | 2 | "deviation" should read --direction-- |

Signed and Sealed this

Twenty-eighth Day of December, 1993

Attest:

BRUCE LEHMAN

Attesting Officer

Commissioner of Patents and Trademarks